United States Patent [19]

Reissenweber et al.

[11] Patent Number: 4,788,324

[45] Date of Patent: Nov. 29, 1988

[54] PREPARATION OF O-(1-METHOXY-2-CHLORO)-ETHOXYPHENYL N-METHYLCARBAMATE

[75] Inventors: Gernot Reissenweber, Boehl-Iggelheim; Siegfried Kersten, Frankenthal; Detlef Doehnert, Ludwigshafen, all of Fed. Rep. of Germany

[73] Assignee: BASF Aktiengesellschaft, Fed. Rep. of Germany

[21] Appl. No.: 102,290

[22] Filed: Sep. 25, 1987

Related U.S. Application Data

[63] Continuation of Ser. No. 794,456, Nov. 4, 1985.

[30] Foreign Application Priority Data

Nov. 10, 1984 [DE] Fed. Rep. of Germany ....... 3441108

[51] Int. Cl.$^4$ ............................................ C07C 175/04
[52] U.S. Cl. ..................................................... 560/132
[58] Field of Search ........................................ 560/132

[56] References Cited

U.S. PATENT DOCUMENTS

| | | | |
|---|---|---|---|
| 3,962,316 | 6/1976 | Kiehs et al. | 560/137 |
| 4,537,986 | 8/1985 | Reissenweber et al. | 560/132 |

OTHER PUBLICATIONS

Loeffler et al., Derwent Abstract No. 35128A (abstract of DE 2650828).
Kirk–Othmer, Encyclopedia of Chemical Technology, 2nd ed., vol. 2, 1963, pp. 103–105, 110–112 and 127–133.
Noller, Chemistry of Organic Compounds, 2nd ed., 1957, pp. 233–237 QD 253 N65.
Liebigs Ann. Chem. 300 (1898) p. 135.
Liebigs Ann. Chem. 362 (1949) p. 205.
J. prakt. Chem. 313 (1971) p. 626.

*Primary Examiner*—Paul F. Shaver
*Assistant Examiner*—Bruce D. Gray
*Attorney, Agent, or Firm*—Keil & Weinkauf

[57] ABSTRACT

O-(1-Methoxy-2-chloro)ethoxyphenyl N-methylcarbamate is prepared by reacting pyrocatechol carbonate with methylamine and then reacting the resulting pyrocatechol monomethylcarbamate with 1,2-dichloroethyl methyl ether in the presence of a secondary amine.

4 Claims, No Drawings

PREPARATION OF O-(1-METHOXY-2-CHLORO)-ETHOXYPHENYL N-METHYLCARBAMATE

This application is a continuation of application Ser. No. 794,456, filed on Nov. 4, 1985.

The present invention relates to a process for the preparation of o-(1-methoxy-2-chloro)-ethoxyphenyl N-methylcarbamate, an insecticidal active ingredient, by reacting pyrocatechol carbonate with methylamine and then reacting the resulting pyrocatecol monomethylcarbamate with 1,2-dichloroethyl methyl ether in the presence of a secondary amine and, preferably, of a solvent.

Processes for the preparation of pyrocatechol carbamates by reacting pyrocatechol carbonate with a primary or secondary amine have been disclosed in, for example, Liebigs Ann. Chem. 300 (1898), 135; ibid. 362 (1949), 205, J. prakt. Chem. 313 (1971), 626 and German Laid-Open Application DOS No. 2,650,828 (also see Houben-Weyl, 4th edition, volume 8, pages 139–140). A reaction of pyrocatechol carbonate with methylamine in the presence of a tertiary amine to give the corresponding carbamate is also known (DE-A No. 32 27 931).

The reaction of pyrocatechol monomethylcarbamate with 1,2-dichloroethyl methyl ether in the presence of a tertiary amine as an HCl acceptor is described in DE-A No. 22 31 249 and 26 50 828.

Particularly for industrial-scale production, the conventional processes have a number of disadvantages, especially with regard to the alkylation step. When the tertiary amines described in German Laid-Open Application DOS No. 2,650,828 are used as HCl acceptors in the reaction of pyrocatechol carbamate with 1,2-dichloroethyl methyl ether, long reaction times are required. Hence, economically acceptable conversion is achieved at the expense of a good space-time yield.

Furthermore, the yields obtained are not particularly high and the purity and stability of the end product are unsatisfactory.

It is an obiect of the present invention to provide a process for the preparation of o-(1-methoxy-2-chloro)-ethoxyphenyl N-methylcarbamate which takes place smoothly.

We have found that this object is achieved, according to the invention, if both the reaction of pyrocatechol carbonate with methylamine and the subsequent conversion of the pyrocatechol monomethyl carbamate are carried out in the presence of a secondary amine $HNR_2$, where R is alkyl which is branched in the $\alpha$-position or is a cycloaliphatic radical, e.g. diisopropylamine, dicyclohexylamine or N-isopropylcyclohexylamine.

In view of the prior art, the results are surprising. For example, it is known that the reaction of pyrocatechol carbonate with secondary amines gives the corresponding pyrocatechol carbamates (J. prakt. Chem. 313 (1971) 26). It is also known that $\alpha$-haloethers react with secondary amines to give the corresponding 0, N-acetals in high yields (Ann. 702 (1967/68) and Chem. Ber. 100 (1967) 7, 2131).

On the basis of the prior art, it was to be expected that, in the novel process, the secondary amine used would react with the pyrocatechol carbonate in the first stage, and alkylation of the amine by the 1,2-dichloroethyl methyl ether would take place in the second stage, i.e. a low overall yield and heterogeneous product mixture were to be expected.

In fact, the reaction of pyrocatechol carbonate with methylamine in the presence of not less than 1 mol equivalent of the abovementioned secondary amines gives pyrocatechol monomethylcarbamate in a yield of 98–99%. The subsequent reaction of the reaction mixture with 1,2-dichloroethyl methyl ether in turn takes place with a yield of above 90%. Compared with the reaction with tertiary amines, the conversion takes place substantially more rapidly (on the bas-is of experience, from eight to ten times faster) and with better selectivity, and consequently a purer and more stable end product is obtained.

The reaction of the first stage takes place at an equate rate at from $-20°$ to $+80°$ C., preferably from $0°$ to $+40°$ C., and that in the second stage takes place sufficiently rapidly at from $0°$ to $+80°$ C., preferably from $+20°$ to $+40°$ C.

The solvents used are chlorohydrocarbons such as dichloromethane, dichloroethane or dichloroethylene, or dipolar aprotic solvents. However, such dipolar aprotic solvents, such as tetrahydrofuran, dimethylformamide or dimethyl sulfoxide, are generally more expensive.

Suitable secondary amines are the amines of the general formula $H-N(R)_2$, in which the radicals R may be identical or different and are each alkyl which is branched in the $\alpha$-position or a cycloaliphatic radical. Examples of suitable compounds are diisopropylamine, dicyclohexylamine, dicyclopentylamine, cyclohexylisopropylamine and di-sec.-butylamine. The amount of secondary amine added is advantageously from 1 to 2, preferably from 1.2 to 1.5, moles per mole of carbonate, i.e. a stoichiometric excess of amine is preferably used.

Advantageously, the pyrocatechol carbonate is initially introduced together with the secondary amine in the desired solvent, and methylamine is added gradually with vigorous mixing (back-mixing). When the process is carried out industrially, it is advantageous to react a solution of pyrocatechol carbonate in the secondary amine continuously with methylamine in a circulation apparatus or a reaction tube. Pyrocatechol carbonate and the secondary amine may furthermore each be fed in as a solution and reacted with methylamine. 1,2-Dichloroethyl methyl ether is then added to the reaction mixture with vigorous stirring. The amount added is advantageously from 1 to 2, preferably from 1.2 to 1.4, moles per mole of carbonate. In this case, the reaction in the second stage can be carried out in a system with intermittent back-mixing or without back-mixing.

Where a chlorohydrocarbon, e.g. methylene chloride, is used, the desired product can be isolated from the reaction mixture by first removing the resulting amine hydrochoride by extraction with water and then evaporating the solvent. When the procedure is carried out industrially, it is advantageous if the active ingredient is precipitated from the solution freed from amine hydrochloride, precipitation being effected by adding a non-polar hydrocarbon, e.g. n-hexane or n-heptane, and is then isolated by a conventional method, such as filtration or centrifuging. Where a dipolar aprotic solvent, such as dimethylformamide, is employed, the active ingredient can be precipitated by adding water and isolated as indicated above.

EXAMPLE

A solution consisting of 2.3 of methylene chloride, 550 g of pyrocatechol carbonate and 600 g of diisopropylamine was fed at a rate of 2,100 g/h (about 1.8 l/h) into a circulation apparatus having a capacity of 250 ml, and at the same time 67 g/h of methylamine were introduced via a second feed. The temperature was kept at 28°–32° C. The solution flowing out was passed into a stirred kettle cascade consisting of two stirred flasks, each having a capacity of about 2, l where 330 g/h of 95% pure 1,2-dichloroethyl methyl ether were added to the solution at from 30° to 35° C. The overflow or the level in the cascade was adjusted so that the mean residence time of the solution was 1.5 hours. Working up was carried out as follows: the amount of solution obtained in 1 hour, about 2 l, was extracted with 1.5 l of 0.15 percent strength aqueous formic acid and then with 2 l of 0.6 percent strength sodium hydroxide solution. A total of 14 l of n-heptane were then added to the vigorously stirred methylene chloride phase at 15° C., and the precipitated product was filtered off under suction and dried. 550 g (92%, based on pyrocatechol carbonate used) of o-(1-methoxy-2-chloro)ethoxyphenyl N-methylcarbamate of melting point 80° C. were obtained. The purity according to HPLC was 98.6%.

We claim:

1. A process for the preparation of o-(1-methoxy-2-chloro)-ethoxyphenyl N-methylcarbamate by reacting pyrocatechol carbonate with methylamine and then reacting the resulting pyrocatechol monomethylcarbamate with 1,2-dichloroethyl methyl ether in the presence of an amine, wherein both the reaction of pyrocatechol carbonate with methylamine and the subsequent conversion of the pyrocatechol monomethylcarbamate are carried out in the presence of a secondary amine $HNR_2$ selected from the group consisting of diisopropylamine and dicyclohexylamine.

2. A process of claim 1, wherein the reaction is carried out in the presence of a stoichiometric excess, based on pyrocatechol carbonate, of a secondary amine.

3. A process of claim 2, wherein the excess is not more than 1 mole per mole.

4. A process of claim 1, wherein the reaction is carried out continuously in such as way that the first stage takes place with back-mixing and the second stage takes place in a stirred kettle cascade or, after initial back-mixing, in a tube reactor.

* * * * *